US006653422B2

(12) United States Patent
Freeman et al.

(10) Patent No.: US 6,653,422 B2
(45) Date of Patent: *Nov. 25, 2003

(54) FOLDABLE OPHTHALMIC AND OTORHINOLARYNGOLOGICAL DEVICE MATERIALS

(75) Inventors: Charles Freeman, Arlington, TX (US); Douglas C. Schlueter, Fort Worth, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/350,993

(22) Filed: Jan. 24, 2003

(65) Prior Publication Data

US 2003/0130460 A1 Jul. 10, 2003

Related U.S. Application Data

(63) Continuation of application No. 09/645,669, filed on Aug. 23, 2000, now Pat. No. 6,528,602.
(60) Provisional application No. 60/152,622, filed on Sep. 7, 1999.

(51) Int. Cl.$^7$ .............................. C08F 32/08; A61F 2/16
(52) U.S. Cl. ................... 526/259; 526/286; 526/292.3; 526/292.5; 526/307.5; 526/312; 526/313; 526/320; 526/323.1; 526/323.2; 526/319; 526/328; 623/6.11; 623/6.54
(58) Field of Search .............................. 623/6.11, 6.54; 351/159; 526/259, 292.5, 307.5, 312, 323.1, 292.3, 323.2, 286, 313, 320

(56) References Cited

U.S. PATENT DOCUMENTS

| | | | |
|---|---|---|---|
| 3,850,892 A | 11/1974 | Shen et al. ............... 260/80.72 |
| 4,036,814 A | 7/1977 | Howes et al. .................. 260/47 |
| 4,260,954 A | 4/1981 | Crooks ........................ 330/85 |
| 4,267,295 A | 5/1981 | Gallop et al. ................ 526/264 |
| 4,304,895 A | 12/1981 | Loshaek ....................... 526/313 |
| 4,393,184 A | 7/1983 | Tarumi et al. ............... 526/261 |
| 4,405,773 A | 9/1983 | Loshaek et al. ............. 526/317 |
| 4,452,776 A | 6/1984 | Refojo ......................... 424/81 |
| 4,518,756 A | 5/1985 | Yoshida et al. ............. 526/313 |
| 4,528,311 A | 7/1985 | Beard et al. .................. 524/71 |
| 4,529,747 A | 7/1985 | Kato et al. .................. 523/108 |
| 4,620,954 A | 11/1986 | Singer et al. ................. 264/1.4 |
| 4,676,792 A | 6/1987 | Praeger ........................ 623/6 |
| 4,704,006 A | 11/1987 | Sakagami et al. .......... 350/409 |
| 4,761,438 A | 8/1988 | Komiya et al. .............. 523/106 |
| 4,834,750 A | 5/1989 | Gupta ........................... 623/6 |
| 5,019,100 A | 5/1991 | Hennink et al. ................ 623/6 |
| 5,269,813 A | 12/1993 | Yoshida et al. ................ 623/6 |
| 5,290,892 A | 3/1994 | Namdaran et al. .......... 526/259 |
| 5,331,073 A | 7/1994 | Weinschenk, III et al. . 526/264 |
| 5,359,021 A | 10/1994 | Weinschenk, III et al. . 526/264 |
| 5,416,180 A | 5/1995 | Yokoyama et al. .......... 526/245 |
| 5,433,746 A | 7/1995 | Namdaran et al. ............. 623/6 |
| 5,507,805 A | 4/1996 | Koeniger ....................... 623/6 |
| 5,594,085 A | 1/1997 | Lai .............................. 526/302 |
| 5,654,350 A | 8/1997 | Nunez et al. ................ 523/106 |
| 5,693,095 A | 12/1997 | Freeman et al. ................ 623/6 |
| 5,821,306 A | 10/1998 | Hodd .......................... 525/228 |
| RE36,150 E | 3/1999 | Gupta ............................ 623/6 |
| 5,891,931 A | 4/1999 | Leboeuf et al. ............... 522/64 |
| 5,922,821 A | 7/1999 | LeBoeuf et al. ............. 526/286 |
| 6,271,281 B1 | 8/2001 | Liao et al. ................... 523/106 |
| 6,281,319 B1 | 8/2001 | Mentak ....................... 526/319 |
| 6,528,602 B1 * | 3/2003 | Freeman et al. ............. 526/259 |

FOREIGN PATENT DOCUMENTS

| | | |
|---|---|---|
| EP | 0 273 710 | 7/1988 |
| EP | 0 136 807 | 12/1990 |
| EP | 0 485 197 | 5/1992 |
| EP | 0 391 452 | 1/1994 |
| EP | 0 898 972 A2 | 3/1999 |
| EP | 1 030 194 A1 | 8/2000 |
| JP | 5 9136-310 A | 1/1983 |
| JP | 6 0202-110 A | 3/1984 |
| JP | 6 310 9866 | 5/1988 |
| JP | 11056999 A | 3/1999 |
| WO | WO 95/11279 | 4/1995 |
| WO | WO 96/11235 | 4/1996 |
| WO | WO 97/24382 | 7/1997 |
| WO | WO 99/11303 | 3/1999 |
| WO | WO 99/18139 | 4/1999 |
| WO | WO 99/53347 | 10/1999 |
| WO | WO 00/26698 | 5/2000 |
| WO | WO 00/34804 | 6/2000 |
| WO | WO 00/60383 | 10/2000 |
| WO | WO 00/79312 A1 | 12/2000 |

OTHER PUBLICATIONS

Barrett, "A New Hydrogel Intraocular Lens Design," *J. Cataract Refract. Surg.*, vol. 20, pp. 18–25 (1994).
Koch, D. *Foldable Intraocular Lenses*, slack Incorporated, Thorofare, NJ (1993), Chapter 8, "Alcon AcrySof® Acrylic Intraocular Lens," pp. 161–177.
Koch, D. *Foldable Intraocular Lenses*, slack Incorporated, Thorofare, NJ (1993), Chapter 8, "ORC MemoryLens™ A Thermoplastic IOL," pp. 197–212.
Sandner et al., "Die Medienabhängigkeit der alkalischen Hydrolyse von Methylmethacrylat–Polymeren," *Die Angewandte Makromolekulare Chemie*, vol. 115, pp. 207–219 (1983).

* cited by examiner

*Primary Examiner*—Tatyana Zalukaeva
(74) *Attorney, Agent, or Firm*—Patrick M. Ryan

(57) ABSTRACT

Disclosed are soft, high refractive index, acrylic materials having an elongation of at least 150%. These materials, especially useful as intraocular lens materials, contain an aryl acrylic hydrophobic monomer as the single principal device-forming monomer. In addition to their use as intraocular lens materials, the present materials are also suitable for use in other ophthalmic or otorhinolaryngological devices, such as contact lenses, keratoprostheses, corneal inlays or rings; otological ventilation tubes and nasal implants.

16 Claims, No Drawings

FOLDABLE OPHTHALMIC AND OTORHINOLARYNGOLOGICAL DEVICE MATERIALS

This application is a continuation of U.S. Ser. No. 09/645,669, filed Aug. 23, 2000, now U.S. Pat. No. 6,528,602 which claims priority from U.S. Provisional Application, U.S. Ser. No. 60/152,622 filed Sep. 7, 1999.

FIELD OF THE INVENTION

This invention is directed to acrylic device materials. In particular, this invention relates to soft, high refractive index acrylic device materials particularly suited for use as intraocular lens ("IOL") materials.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than silicone materials.

U.S. Pat. No. 5,290,892 discloses high refractive index, acrylic materials suitable for use as an IOL material. These acrylic materials contain, as principal components, two aryl acrylic monomers. They also contain a cross-linking component. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable ophthalmic lens materials comprising a total of at least 90% by weight of only two principal lens-forming monomers. One lens-forming monomer is an aryl acrylic hydrophobic monomer. The other lens-forming monomer is a hydrophilic monomer. The lens materials also comprise a cross-linking monomer and optionally comprise a UV absorber, polymerization initiators, reactive UV absorbers and reactive blue-light absorbers.

SUMMARY OF THE INVENTION

Improved soft, foldable acrylic materials which are particularly suited for use as IOLs, but which are also useful as other ophthalmic or otorhinolaryngological devices, such as contact lenses, keratoprostheses, corneal rings or inlays, otological ventilation tubes and nasal implants have now been discovered. These materials contain only one principal lens-forming component: an aryl acrylic hydrophobic monomer. The materials of the present invention comprise at least about 80% by weight of the principal monomeric component. The remainder of the material comprises a cross-linking monomer and optionally one or more additional components selected from the group consisting of UV-light absorbing compounds and blue-light absorbing compounds.

Among other factors, the present invention is based on the finding that acrylic copolymers suitable for use as foldable IOL materials can be synthesized using only one principal aryl acrylic hydrophobic monomer, reducing or eliminating difficulties, such as physico/chemical heterogeneity, associated with curing copolymers that contain two or more principal device-forming monomers.

DETAILED DESCRIPTION OF THE INVENTION

The ophthalmic or otorhinolaryngological device materials of the present invention comprise only one principal device-forming monomer. For convenience, the device-forming monomer may be referred to as a lens-forming monomer, particularly with reference to an IOL. The materials of the present invention, however, are also suitable for use as other ophthalmic or otorhinolaryngological devices such as contact lenses, keratoprostheses, corneal inlays or rings, otological ventilation tubes and nasal implants.

The aryl acrylic hydrophobic monomers suitable for use as the sole lens-forming monomer in the materials of the present invention have the formula

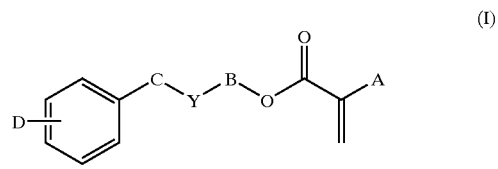

wherein: A is H, $CH_3$, $CH_2CH_3$, or $CH_2OH$;
B is $(CH_2)_m$ or $[O(CH_2)_2]_n$;
C is $(CH_2)_w$;
m is 2–6;
n is 1–10;
Y is nothing, O, S, or NR, provided that if Y is O, S, or NR, then B is $(CH_2)_m$;
R is H, $CH_3$, $C_nH_{2n+1}$ (n=1–10), iso-$OC_3H_7$, $C_6H_5$, or $CH_2C_6H_5$;
w is 0–6, provided that m+w≦8; and
D is H, $C_1$—$C_4$ alkyl, $C_1$–$C_4$ alkoxy, $C_6H_5$, $CH_2C_6H_5$ or halogen.

Preferred aryl acrylic hydrophobic monomers for use in the materials of the present invention are those wherein A is $CH_3$, B is $(CH_2)$m, m is 2–5, Y is nothing or O, w is 0–1, and D is H. Most preferred are 4-phenylbutyl methacrylate, 5-phenylpentyl methacrylate, 2-benzyloxyethyl methacrylate, and 3-benzyloxypropyl methacrylate.

Monomers of structure I can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion.

Alternative synthesis schemes involve adding methacrylic acid to the conjugate alcohol and catalyzing with a carbodiimide or mixing the conjugate alcohol with methacryloyl chloride and a base such as pyridine or triethylamine.

The materials of the present invention comprise a total of at least about 80%, preferably at least about 85%, by weight or more of the principal lens-forming monomer.

The copolymer materials of the present invention are cross-linked. The copolymerizable cross-linking agent used in the copolymers of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2=C(CH_3)C(=O)O—(CH_2CH_2O)_n—C(=O)C(CH_3)=CH_2$ where n=1–50; and $CH_2=C(CH_3)C(=O)O(CH_2)_tO—C(=O)C(CH_3)=CH_2$ where t=3–20; and their corresponding acrylates. The most preferred cross-linking monomer is $CH_2=C(CH_3)C(=O)O—(CH_2CH_2O)_n—C(=O)C(CH_3)=CH_2$ where n is such that the number-average molecular weight is about 400, about 600, or, most preferably, about 1000.

The chosen cross-linking agent should be soluble in the chosen monomer of structure I to minimize curing problems. When n approaches the upper end of the range of 1–50, the $CH_2=C(CH_3)C(=O)O—(CH_2CH_2O)_n—C(=O)C(CH_3)=CH_2$ cross-linker may not be soluble at desired levels in some monomers of structure I even with the aid of heat or sonication.

Generally, only one cross-linking monomer will be present in the device materials of the present invention. In some cases, however, combinations of cross-linking monomers may be desirable. If combinations of two or more types of cross-linking agents are used, none of the cross-linking agents may be $CH_2=C(CH_3)C(=O)O—(CH_2CH_2O)_n—C(=O)C(CH_3)=CH_2$ wherein n=2–50.

Generally, the total amount of the cross-linking component is at least 0.1% by weight and, depending on the identity and concentration of the remaining components and the desired physical properties, can range to about 20% by weight. The preferred concentration range for the cross-linking component is 0.1–15% by weight.

In addition to the aryl acrylic hydrophobic lens-forming monomer and the cross-linking component, the lens material of the present invention may also contain a total of up to about 10% by weight of additional components which serve other purposes, such as reactive UV and/or blue-light absorbers.

A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1–5% (weight).

Suitable reactive blue-light absorbing compounds are those described in U.S. Pat. No. 5,470,932, the entire contents of which are hereby incorporated by reference. Blue-light absorbers are typically present in an amount from about 0.01–0.5% (weight).

Suitable polymerization initiators include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadoxe® from Akzo Chemicals Inc., Chicago, Ill.). Particularly in cases where the lens material does not contain a blue-light absorbing chromophore, preferred photoinitiators include benzoylphosphine oxide photoinitiators, such as the blue-light initiator 2,4,6-trimethyl-benzoyidiphenylphosphine oxide, commercially available as Lucirin® TPO from BASF Corporation (Charlotte, N.C.). Initiators are typically present in an amount of about 5% (weight) or less.

The identity and amount of the principal lens-forming monomer described above and the identity and amount of any additional components are determined by the desired properties of the finished ophthalmic lens. Preferably, the ingredients and their proportion are selected so that the acrylic lens materials of the present invention possess the following properties, which make the materials of the present invention particularly suitable for use in IOLs which are to be inserted through incisions of 5 mm or less.

The lens material preferably has a refractive index in the dry state of at least about 1.50 as measured by an Abbe' refractometer at 589 nm (Na light source). For a given optic diameter, optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the lens material, which affects the material's folding and unfolding characteristics, is preferably below about 25° C., and more preferably below about 15° C. Tg is measured by differential scanning calorimetry at 10° C./min., and is determined at the midpoint of the transition of the heat flux curve.

The lens material will have an elongation of at least 150%, preferably at least 200%, and most preferably at least 300%. This property indicates that the lens generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using a tensile tester. The grip distance is set at 14 mm and a crosshead speed is set at 500 mm/minute and the sample is pulled to failure. The elongation (strain) is reported as a fraction of the displacement at failure to the original grip distance. The modulus is calculated as the instantaneous slope of the stress-strain curve at a selected strain. Stress is calculated at the maximum load for the sample, typically the load when the sample breaks, assuming that the initial area remains constant. This stress is recorded as "tensile strength" in the examples below.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

The invention will be further illustrated by the following examples, which are intended to be illustrative, but not limiting. Example 1: Synthesis of 4-phenylbutyl methacrylate.

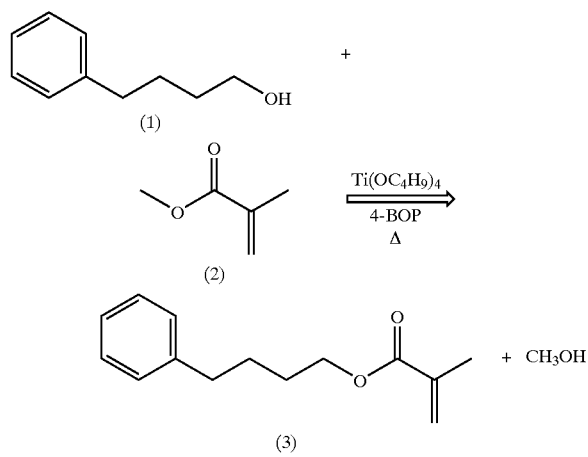

A three neck round bottom flask containing a teflon coated magnetic stirring bar was successively charged with 120 mL (1.09 mol) of methyl methacrylate (2), 5.35 g (0.015 mol) of titanium tetrabutoxide (Ti(OC$_4$H$_9$)$_4$), 60 mL (0.39 mol) of 4-phenyl-1-butanol (1), and 14.6 g (0.073 mol) of 4-benzyloxyphenol (4-BOP). An addition funnel, thermometer, and a short path still head with thermometer and receiver flask were placed in the flask necks. The flask was placed in an oil bath and the temperature was increased until distillation began. Methyl methacrylate (2) was placed in the addition funnel and was added dropwise at the same rate as the distillate. The reaction mixture was heated for 4 hours and then cooled to room temperature. The crude product was vacuum distilled to isolate 62.8 g (0.29 mol, 74%) of 4-phenylbutyl methacrylate (3) as a clear, colorless liquid. Example 2: Synthesis of 3-benzyloxypropyl methacrylate.

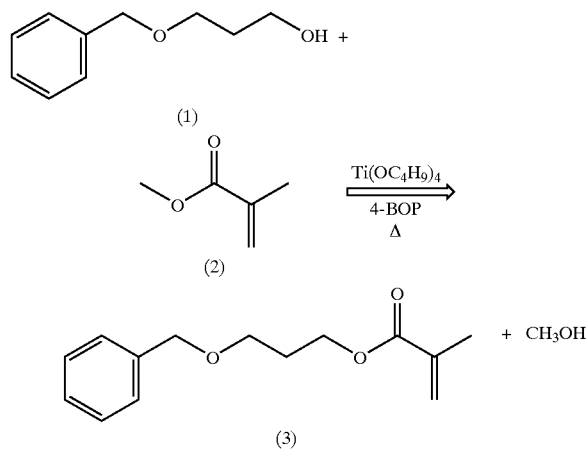

A three neck round bottom flask containing a teflon coated magnetic stirring bar was successively charged with 95 mL (0.884 mol) of methyl methacrylate (2), 4.22 g (0.012 mol) of titanium tetrabutoxide (Ti(OC$_4$H$_9$)$_4$), 50 mL (0.316 mol) of 3-benzyloxy-1-propanol (1), and 14.6 g (0.073 mol) of 4-benzyloxyphenol (4-BOP). An addition funnel, thermometer, and a short path still head with thermometer and receiver flask were placed in the flask necks. The flask was placed in an oil bath and the temperature was increased until distillation began. Methyl methacrylate (2) was placed in the addition funnel and was added dropwise at the same rate as the distillate. The reaction mixture was heated for 4 hours and then cooled to room temperature. The crude product was vacuum distilled to isolate 36.5 g (0.156 mol, 49%) of 3-benzyloxypropyl methacrylate (3) as a clear, colorless liquid.

Examples 3–29, shown below in Tables 1–4, illustrate of the materials of the present invention. Each of the formulations of Examples 3–29 are prepared as follows. After combining the formulation components as listed in Tables 1–4, each formulation is mixed by agitation and then injected into a polypropylene 25×12×1 mm slab mold. To make slabs, the cavity in the bottom portion of the slab mold is filled to capacity with the formulation and then the top is placed on strictly as a seal. The molds can either be filled under an inert nitrogen or standard laboratory atmosphere. To maintain the mold geometry during curing, spring clamps are used on the molds. The clamped molds are placed in a forced air oven and cured by heating to 70–80° C., holding at 70–80° C. for one hour, then heating to approximately 100–110° C. and holding at approximately 100–110° C. for two hours. At the end of polymerization period, the molds are opened and the cured intraocular lenses or polymer slabs are removed and extracted in acetone to remove any materials not bound to the cross-linked network.

Physical property data shown for the cured materials in Tables 1–4 were assessed (according to the methods referred to above). Unless indicated otherwise, all ingredient amounts shown below are listed as % by weight. The following abbreviations are used in Tables 1–4:

PEMA: 2-phenylethyl methacrylate
PPrMA: 3-phenylpropylmethacrylate
PBMA: 4-phenylbutylmethacrylate
BEEMA: benzyloxyethoxyethyl methacrylate
BEMA: 2-benzyloxyethyl methacrylate
BPMA: 3-benzyloxypropyl methacrylate
PPMA: 5-phenylpentyl methacrylate
BBMA: 4-benzyloxybutyl methacrylate
PEO 1000: polyethylene glycol 1000 dimethacrylate
PEO 600: polyethylene glycol 600 dimethacrylate
PEO 400: polyethylene glyclo 400 dimethacrylate
EGDMA: ethylene glycoldimethacrylate
t-BPO: t-butyl (peroxy-2-ethyl)hexanoate
BPO: benzoyl peroxide

TABLE 1

| Example No. | PEMA | PPrMA | PBMA | PEO 1000 | EGDMA | t-BPO | % Elongation | Tg (° C.) |
|---|---|---|---|---|---|---|---|---|
| 3 | 85 | | | 15 | | 1 | 304 | — |
| 4 | | 99 | | | 1 | 1 | 172 | 15 |

TABLE 1-continued

| Example No. | PEMA | PPrMA | PBMA | PEO 1000 | EGDMA | t-BPO | % Elongation | Tg (° C.) |
|---|---|---|---|---|---|---|---|---|
| 5 | | 85 | | 15 | | 1 | 753 | −10 |
| 6 | | | 99 | | 1 | 1 | 583 | 0 |
| 7 | | | 85 | 15 | | 1 | 619 | −24 |

TABLE 2

| | Examples | | | | | | |
|---|---|---|---|---|---|---|---|
| Component | 8 | 9 | 10 | 11 | 12 | 13 | 14 |
| BEMA | — | — | — | — | — | 89.9 | — |
| PBMA | — | — | — | — | — | — | 90.0 |
| BPMA | 94.7 | 90 | — | 99.6 | — | — | — |
| PPMA | — | — | 89.7 | — | — | — | — |
| BBMA | — | — | — | — | 89.9 | — | — |
| PEO 1000 | 5.3 | 10 | 10.3 | — | 10.1 | 10.1 | 10.1 |
| EGDMA | — | — | — | 0.4 | — | — | — |
| t-BPO | 1.4 | 1.5 | 1.4 | 1.6 | 1.6 | 1.3 | 1.4 |
| Tensile strength (MPa) | 3.37 | 2.83 | 2.02 | 3.07 | 1.11 | 6.46 | 4.195 |
| % Strain | 900 | 659 | 515 | 974 | 440 | 815 | 696 |
| Young's modulus (MPa) | 0.67 | 0.62 | 0.76 | 1.02 | 0.33 | 1.89 | 2.00 |
| 100% modulus (MPa) | 0.45 | 0.42 | 0.51 | 0.59 | 0.22 | 1.07 | 0.99 |
| RI (dry) | 1.539 | 1.534 | 1.533 | 1.543 | 1.531 | 1.541 | 1.535 |

TABLE 3

| | Examples | | | | | | | | |
|---|---|---|---|---|---|---|---|---|---|
| Component | 15 | 16 | 17 | 18 | 19 | 20 | 21 | 22 | 23 |
| PBMA | 89.75 | 85.02 | 79.97 | 94.95 | 89.82 | 85.03 | 94.99 | 89.89 | 84.96 |
| PEO 400 | 10.25 | 14.98 | 20.03 | — | — | — | — | — | — |
| PEO 600 | — | — | — | 5.05 | 10.18 | 14.97 | — | — | — |
| PEO 1000 | — | — | — | — | — | — | 5.01 | 10.11 | 15.04 |
| BPO | 0.98 | 0.96 | 0.95 | 0.98 | 0.95 | 0.96 | 1.04 | 0.95 | 0.97 |
| Tensile Strength (MPA) | 8.23 | 8.6 | 8.74 | 6.55 | 6.33 | 514 | 6.17 | 5.62 | 4.35 |
| % Strain | 444 | 378 | 325 | 881 | 707 | 562 | 1051 | 875 | 699 |
| Young's modulus (MPA) | 6.59 | 5.78 | 5.56 | 3.85 | 2.82 | 1.77 | 4.05 | 1.92 | 1.24 |
| 100% modulus (MPA) | 3.47 | 3.34 | 3.32 | 2.28 | 1.55 | 1.12 | 2.06 | 1.12 | 0.77 |
| Tg(° C.) | 5 | 4 | −1 | −1 | −5 | — | — | — | — |

TABLE 4

| | Examples (Ingredients shown in % w/w) | | | | | | | |
|---|---|---|---|---|---|---|---|---|
| Component | 24 | 25 | 26 | 27 | 28 | 29 | 30 | 31 |
| BEEMA | — | — | — | — | — | — | 99.6 | 90.0 |
| PPrMA | 85.03 | — | — | 85.00 | — | — | — | — |
| PBMA | — | 85.02 | — | — | 84.94 | — | — | — |
| PPMA | — | — | 85.06 | — | — | 85.00 | — | — |
| PEO 600 | 14.97 | 14.98 | 14.94 | — | — | — | — | — |
| PEO 1000 | — | — | — | 15.00 | 15.06 | 15.00 | — | 10.0 |
| EGDMA | — | — | — | — | — | — | 0.6 | — |
| BPO | 1.00 | 1.01 | 0.99 | 1.01 | 1.01 | 1.01 | — | — |
| t-BPO | — | — | — | — | — | — | 1.1 | 1.2 |
| Tensile Strength (MPA) | 8.34 | 4.24 | 2.67 | 6.15 | 3.35 | 2.05 | 1.56 | 1.22 |
| % Strain | 502 | 486 | 390 | 662 | 582 | 402 | 468 | 294 |
| Youngs (MPA) | 5.48 | 1.38 | 0.85 | 2.41 | 0.88 | 0.67 | 0.32 | 0.51 |
| 100% (MPA) | 3.09 | 0.96 | 0.57 | 1.41 | 0.63 | 0.48 | 0.24 | 0.36 |
| Tg (° C.) | — | — | — | — | — | — | −23.2 | −26.7 |

We claim:

1. A polymeric ophthalmic or otorhinolaryngological device material having an elongation of at least 150%, consisting essentially of a single device-forming monomer and at least one cross-linking monomer, optionally a reactive UV absorber and optionally a reactive blue-light absorber, wherein the single device-forming monomer is pr sent in an amount of at least about 80% by weight and is an aryl acrylic hydrophobic monomer of the formula

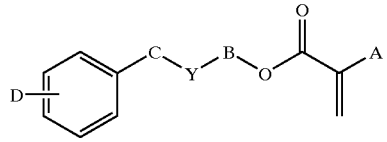

(I)

wherein: A is $CH_3$, $C_2CH_3$, or $CH_2OH$;

B is $(CH_2)_m$ or $(O(CH_2)_2)_n$;

m is 2–6;

n is 1–10;

Y is nothing, O, S, or NR, provided that if Y is O, S, or NR, then B is $(CH_2)_m$;

R is H, $CH_3$, $C_nH_{2n+1}$(n=1–10), iso-$OC_3H_7$, $C_6H_5$, or $CH_2C_6H_5$;

w is 0–6, provided that m+w≦8; and

D is H, $C_1$—$C_4$ alkyl, $C_1$—$C_4$ alkoxy, $C_6H_5$, or $CH_2C_6H_5$, and provided that if combinations of two or more types of cross-linking agents are used, none of the cross-linking agents may be $CH_2=C(CH_3)C(=O)O-(CH_2CH_2O)_n-C(=O)C(CH_3)=CH_2$ wherein n=2–50.

2. The polymeric ophthalmic or otorhinolaryngological device material of claim 1 wherein A is $CH_3$, B is $(CH_2)_m$, m is 2–5, Y is nothing or O, w is 0–1, and D is H.

3. The polymeric ophthalmic or otorhinolaryngological device material of claim 2 wherein the aryl acrylic hydrophobic monomer is selected from the group consisting of 4-phenylbutyl methacrylate; 5-phenylpentyl methacrylate; 2-benzyloxyethyl methacrylate; and 3-benzyloxypropyl methacrylate.

4. The polymeric ophthalmic or otorhinolaryngological device material of claim 1 further comp sing one or more components selected from the group consisting of reactive U absorbers and reactive blue-light absorbers.

5. The polymeric ophthalmic or otorhinolaryngological device material of claim 1 wherein the material is an ophthalmic device material and has a refractive index of at least 1.50.

6. The polymeric ophthalmic or otorhinolaryngological device material of claim 1 wherein the material has a Tg less than about +25° C.

7. The polymeric ophthalmic or otorhinolaryngological device material of claim 6 wherein the material has a Tg less than about +15° C.

8. The polymeric ophthalmic or otorhinolaryngological device material of claim 1 wherein the material has an elongation of at least 200%.

9. The polymeric ophthalmic or otorhinolaryngological device material of claim 8 wherein the copolymer has an elongation of at least 300%.

10. The polymeric ophthalmic or otorhinolaryngological device material of claim 1 wherein the device is selected from the group consisting of contact lenses; keratoprostheses; corneal inlays or rings; otological ventilation tubes; and nasal implants.

11. The polymeric ophthalmic or otorhinolaryngological device material of claim 1 wherein the cross-linking component comprises one or more cross-linking agents selected from the group consisting of ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2=C(CH_3)C(=O)O-(CH_2CH_2O)_n-C(O)C(CH_3)=CH_2$ where n=1—50; $CH_2=C(CH_3)C(=O)O(CH_2)_tOC(=O)C(CH_3)CH_2$ where t=3–20; and their corresponding acrylates provided that if the device material comprises two or more cross-linking agents, one of the cross-linking agents is $CH_2=C(CH_3)C(=O)O-(CH_2CH_2O)_n-C(=O)C(CH_3)=CH_2$ wherein n=2–50.

12. The polymeric ophthalmic or otorhinolaryngological device material of claim 1 wherein the sin e device-forming monomer is present in an amount of at least about 85% by weight.

13. The polymeric ophthalmic or otorhinolaryngological device material of claim 1 wherein the cross-linking monomer is present in an amount of about 0.01–15% by weight.

14. The polymeric ophthalmic or otorhinolaryngological device material of claim 1 wherein the aryl acrylic hydrophobic monomer is selected from the group consisting of 4-phenylbutyl methacrylate; 5-phenylpentyl methacrylate; 2-benzyloxyethyl methacrylate; and 3-benzyloxypropyl methacrylate; and the cross-linking monomer is $CH_2=C(CH_3)C(=O)O-(CH_2CH_2O)_n-C(=O)C(CH_3)=CH_2$, where n is such that the number average molecular weight of the cross-linking monomer is about 1000.

15. An intraocular lens optic comprising the polymeric device material of claim 1.

16. An intraocular lens optic comprising the polymeric device material of claim 14.

* * * * *